(12) United States Patent
Sanemitsu

(10) Patent No.: US 6,391,826 B1
(45) Date of Patent: May 21, 2002

(54) OPTICALLY ACTIVE URACIL COMPOUNDS

(75) Inventor: Yuzuru Sanemitsu, Kobe (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/471,245

(22) Filed: Dec. 23, 1999

(30) Foreign Application Priority Data

Dec. 25, 1998 (JP) .............................................. 10-370828
Mar. 3, 1999 (JP) .............................................. 11-055560

(51) Int. Cl.[7] .................... C07D 239/54; A01N 43/54

(52) U.S. Cl. ....................................... 504/243; 544/314

(58) Field of Search ............................ 544/314; 504/243

(56) References Cited

U.S. PATENT DOCUMENTS

| | | | |
|---|---|---|---|
| 4,859,229 A | 8/1989 | Wenger et al. ............... | 544/309 |
| 5,602,077 A | 2/1997 | Amuti et al. ................ | 544/311 |

FOREIGN PATENT DOCUMENTS

| | | |
|---|---|---|
| WO | 9829554 A1 | 7/1998 |

OTHER PUBLICATIONS

Eliel, Stereo Chemistry of Carbon Compounds McGraw Hill Book Co (1962) pp. 87–95.*

Wenger et al, Chemical Abstracts, vol. 109, entry 73464 (1988).*

* cited by examiner

*Primary Examiner*—John M. Ford
(74) *Attorney, Agent, or Firm*—Birch, Stewart, Kolasch & Birch, LLP

(57) ABSTRACT

The present invention relates to an optically active uracil compounds of the formula (I):

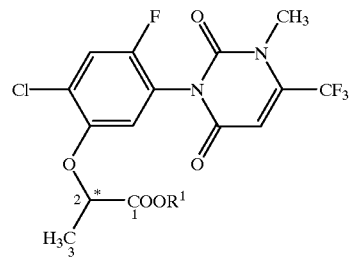

wherein, $R^1$ is C1–C8 alkyl or C3–C8 alkenyl, and * represents an asymmetric carbon atom whose configuration is R. The compounds have excellent herbicidal activity.

19 Claims, No Drawings

OPTICALLY ACTIVE URACIL COMPOUNDS

FIELD OF THE INVENTION

The instant invention relates to optically active uracil compounds and uses thereof.

BACKGROUND ARTS

U.S. Pat. No. 4,859,229 discloses that certain types of uracil compounds have herbicidal activity. However, there is no description concerning whether the herbicidal activities between the optical isomers are the same or different, or which optical isomer is more effective as a herbicidal active ingredient.

Generally speaking, in pesticides field, it is known that some optically active isomers have almost the same activity as their racemic compounds and the other optically active isomers have at most twice activity than their racemic compounds. It seems to be dependent on a structure near the asymmetric carbon in the compound whether the pesticidal activity between the optical isomers is the same or different. However, it is very difficult to estimate a pesticidal activity of an optical isomer without experimentation. When one optical isomer is almost inactive, the other optical isomer is theoretically considered to be effective twice against its racemate, because the racemate contains a half amount of the active optical isomer.

DISCLOSURE OF THE INVENTION

The present invention provides optically active uracil compounds having excellent herbicidal activity. Said uracil compounds are of the formula (I):

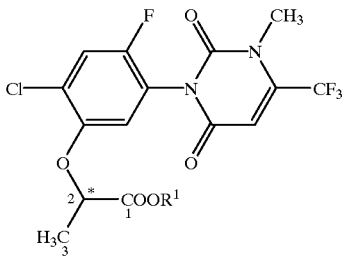

wherein, $R^1$ is C1–C8 alkyl or C3–C8 alkenyl, and * represents an asymmetric carbon atom whose configuration is R, and have excellent herbicidal activity.

DETAILED DESCRIPTION OF THE INVENTION

The present uracil compounds may be essentially pure R isomer in the $2^{nd}$ position of the propionate, namely essentially free from S isomer, or R-rich isomers of the absolute configuration in the $2^{nd}$ position of the propionate, shown in the above formula [hereinafter referred to as the present compound(s)]. In the present invention, essentially pure R isomer means one containing 95% or more R isomer, and R-rich isomer generally means one containing 80% or more R isomer based on the RS mixture.

In the present invention, examples of the C1–C8 alkyl represented by $R^1$ include methyl, ethyl, propyl, isopropyl, butyl, isobutyl, sec-butyl, tert-butyl, amyl, isoamyl, sec-amyl, tert-amyl and hexyl, and examples of the C3–C8 alkenyl represented by $R^1$ include allyl, 1-methyl-2-propenyl, 3-butenyl, 2-butenyl, 3-methyl-2-butenyl and 2-methyl-3-butenyl. Among the present compounds, the compounds wherein $R^1$ is C1–C6 alkyl or C3–C6 alkenyl are preferable.

The present compounds can be produced by methods, for example, shown in the following.

(Production Method 1)

A method of production by reacting a hydroxy compound of the formula (II):

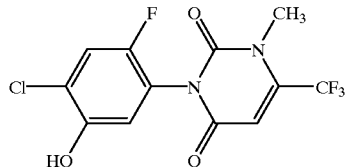

with an S-lactate of the formula (III):

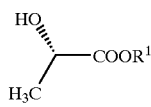

wherein $R^1$ represents the same as defined above.

Said reaction is usually performed in the presence of a triarylphosphine or trialkylphosphine such as triphenylphosphine, triethylphosphine, tributylphosphine and the like, in combination with a di(lower alkyl) azodicarboxylate such as diethyl azodicarboxylate, diisopropyl azodicarboxylate, and the like. Said reaction is usually performed within a solvent, and the range of the reaction temperature is usually –20 to 150° C., preferably 0 to 100° C., and the range of the reaction time is instantaneous to 48 hours. The amount of the S-lactate of the formula (III) used in the reaction is generally 1 to 3 moles, preferably 1 to 1.2 moles, based on 1 mole of the hydroxy compound of the formula (II). The amount of the triarylphosphine or trialkylphosphine is generally 1 to 3 moles, preferably 1 to 1.2 moles, and the amount of the di(lower alkyl) azodicarboxylate is generally 1 to 3 moles, preferably 1 to 1.2 moles, based on 1 mole of the hydroxy compound of the formula (II). Examples of the solvent utilized for the reaction include aliphatic hydrocarbons such as hexane, heptane, ligroin, cyclohexane and petroleum ether; aromatic hydrocarbons such as benzene, toluene and xylene; halogenated aromatic hydrocarbons such as chlorobenzene, dichlorobenzene and benzotrifluoride; ethers such as diethyl ether, diisopropyl ether, dioxane, tetrahydrofuran and ethylene glycol dimethyl ether; and the like, and mixtures thereof. After completing the reaction, for example, by the methods shown below, the objective present compounds can be isolated.

1) The reaction solution is poured into water, that is extracted with an organic solvent, said organic layer is dried and concentrated, and the residue is subjected to chromatography.
2) The reaction solution is concentrated as it is, and the residue is subjected to chromatography.

In addition, it is possible to purify the present compounds by operations such as recrystalization.

The hydroxy compound of the formula (II) can be prepared by the method described in U.S. Pat. No. 4,859,229.

(Production Method 2)

A method of production by reacting a hydroxy compound of the formula (II) with an S-2-chloropropionate of the formula (IV):

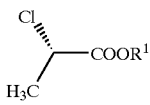

wherein R¹ represents the same as defined above.

Said reaction is usually performed in the presence of a base within a solvent, and the range of the reaction temperature is usually −20 to 100° C., preferably 0 to 40° C., and the range of the reaction time is instantaneous to 240 hours. The amount of the S-2-chloropropionate of the formula (IV) used in the reaction is generally 1 to 2 moles, preferably 1 to 1.2 moles, based on 1 mole of the hydroxy compound of the formula (II). The amount of the base is generally 1 to 3 moles, preferably 1 to 1.2 moles, based on 1 mole of the hydroxy compound of the formula (II). Examples of the base utilized for the reaction include inorganic bases such as lithium carbonate, sodium carbonate, potassium carbonate, sodium hydride and potassium hydride. Examples of the solvent utilized for the reaction include aliphatic hydrocarbons such as hexane, heptane, ligroin, cyclohexane and petroleum ether; aromatic hydrocarbons such as benzene, toluene and xylene; halogenated aromatic hydrocarbons such as chlorobenzene, dichlorobenzene and benzotrifluoride; ethers such as diethyl ether, diisopropyl ether, dioxane, tetrahydrofuran and ethylene glycol dimethyl ether; ketones such as acetone, methyl ethyl ketone, methyl isobutyl ketone, isophorone and cyclohexanone; esters such as ethyl formate, ethyl acetate, butyl acetate and diethyl carbonate; nitriles such as acetonitrile, propionitrile and butyronitrile; acid amides such as formamide, N,N-dimethylformamide and acetamide; sulfur compounds such as dimethyl sulfoxide and sulfolane; and the like, and mixtures thereof. After completing the reaction, for example, by the methods shown below, the objective present compounds can be isolated.
1) The reaction solution is poured into water, that is extracted with an organic solvent, said organic layer is dried and concentrated, and the residue is subjected to chromatography.
2) The reaction solution is concentrated as it is, and the residue is subjected to chromatography.

(Production Method 3)

A method of producing from a carboxylic acid compound of the formula (V):

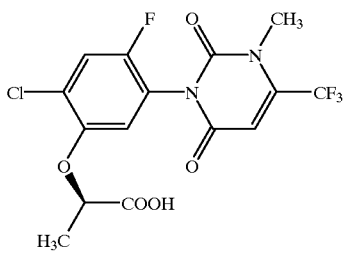

and an alcohol compound of the formula (VI):

wherein R¹ represents the same as defined above.
(Production Method 3-1)

A method of producing by reacting a carboxylic acid compound of the formula (V) with an alcohol compound of the formula (VI) directly.

Said reaction is usually performed in the presence of an acid, without or within a solvent, and the range of the reaction temperature is usually from 20 to 150° C., preferably 50 to 100° C., and the range of the reaction time is usually from instantaneous to 24 hours. The amount of the alcohol compound of the formula (VI) used in the reaction is generally 1 mole to a large excess and the amount of the acid is generally a catalytic amount to 1 mole based on 1 mole of the carboxylic acid compound of the formula (V). Examples of the acid utilized for the reaction include inorganic acid such as sulfuric acid; sulfonic acid such as methanesulfonic acid, trifluoromethanesulfonic acid, p-toluenesulfonic acid, benzenesulfonic acid; ion-exchange resin that is acidic cation resin; and the like. Examples of the solvent utilized for the reaction include aliphatic hydrocarbons such as hexane, heptane, nonane, decane, ligroin, cyclohexane and petroleum ether; halogenated aliphatic hydrocarbons such as methylene chloride, chloroform, carbon tetrachloride, 1,2-dichloroethane and 1,2,3-trichloropropane; aromatic hydrocarbons such as benzene, toluene, xylene and mesitylene; halogenated aromatic hydrocarbons such as chlorobenzene, dichlorobenzene and benzotrifluoride; ethers such as diethyl ether, diisopropyl ether, methyl tert-butyl ether, dioxane, tetrahydrofuran and ethylene glycol dimethyl ether; and the like, and mixtures thereof. After completing the reaction, for example, by the methods shown below, the objective present compounds can be isolated.
1) The reaction solution is poured into water optionally after concentrated, that is extracted with an organic solvent, said organic layer is dried and concentrated, and the residue is subjected to chromatography.
2) The reaction solution is concentrated as it is, and the residue is subjected to chromatography.

The carboxylic acid compound of the formula (V) can be prepared by hydrolysis of the uracil compounds of the formula (I). Therefore, this method serves an ester exchange procedure, and especially it is suitable for the process from methyl or ethyl ester to the other esters.

The hydrolysis may be performed in the presence of an acid and water, and usually within a solvent. The range of the reaction temperature is usually from 20 to 150° C., preferably 70 to 110° C., and the range of the reaction time is usually from instantaneous to 48 hours. The amounts of the acid used in the reaction is generally a catalytic amount to 1 mole, preferably a catalytic amount to 0.2 mole, based on 1 mole of the uracil compound of the formula (I). The amount of the water is generally 1 mole to a large excess, based on 1 mole of the uracil compound of the formula (I). Examples of the acid utilized for the hydrolysis include inorganic acid such as hydrochloric acid and sulfuric acid; sulfonic acid such as methanesulfonic acid, trifluoromethanesulfonic acid, p-toluenesulfonic acid, benzenesulfonic acid; and the like. Examples of the solvent utilized for the reaction include dioxane, tetrahydrofuran and the like. After completing the reaction, for example, by the methods shown below, the objective compound can be isolated.
1) The reaction solution is poured into water optionally after concentrated, that is extracted with an organic solvent, said organic layer is dried and concentrated, and the residue is subjected to chromatography.
2) The reaction solution is concentrated as it is, and the residue is subjected to chromatography.

This method may be modified by known procedures utilizing a dehydration-esterifying agent such as dicyclohexylcarbodiimide.

(Production Method 3-2)

A method of producing by reacting a reactive intermediate such as acid chloride, which can be derived from a carboxylic acid compound of the formula (V), with an alcohol compound of the formula (VI).

Said method may be performed by, after making such into an acid chloride compound by reacting the carboxylic acid compound of the formula (V) with a chlorinating agent (hereinafter referred to as procedure 3-2-1), reacting with the alcohol compound of the formula (VI), in the presence of a base (hereinafter referred to as procedure 3-2-2).

Procedure 3-2-1 is performed without a solvent or within a solvent. The range of the reaction temperature is usually from 0 to 150° C., and the range of the reaction time is usually from instantaneous to 24 hours. The amount of the chlorinating agent offered with the reaction is theoretically 1 mole based on 1 mole of the carboxylic acid compound of the formula (V), but optionally the amount may be changed in the range of 1 mole to an excess as needed with the reaction condition. Examples of the chlorinating agent utilized for the reaction include thionyl chloride, sulfuryl chloride, phosgene, oxalyl chloride, phosphorous trichloride, phosphorous pentachloride and phosphorous oxychloride. Examples of the solvent include aliphatic hydrocarbons such as hexane, heptane, nonane, decane, ligroin, cyclohexane and petroleum ether; aromatic hydrocarbons such as benzene, toluene, xylene and mesitylene; halogenated aliphatic hydrocarbons such as methylene chloride, chloroform, carbon tetrachloride, 1,2-dichloroethane and 1,2,3-trichloropropane; halogenated aromatic hydrocarbons such as chlorobenzene, dichlorobenzene and benzotrifluoride; ethers such as diethyl ether, diisopropyl ether, methyl tert-butyl ether, dioxane, tetrahydrofuran and ethylene glycol dimethyl ether; and the like, and mixtures thereof. After completing the reaction, the reaction solution is usually concentrated under reduced pressure, and the concentrated residue is utilized as it is for procedure 3-2-2.

Procedure 3-2-2 is performed in the presence of a base, and within a solvent or without a solvent. The range of the reaction temperature is usually −20 to 100° C., and the range of the reaction time is usually instantaneous to 24 hours. The amounts of the base and the alcohol compound (VI) used in the reaction are theoretically 1 mole respectively, based on 1 mole of the carboxylic acid compound of the formula (V), but optionally the amounts may be changed in the range of 1 mole to an excess as needed with the reaction condition. Examples of the base utilized for the reaction include inorganic bases such as lithium hydrogencarbonate, sodium hydrogencarbonate, potassium hydrogencarbonate, lithium carbonate, sodium carbonate and potassium carbonate; nitrogen-containing aromatic compounds such as pyridine, quinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine and 5-ethyl-2-methylpyridine; tertiary amines such as triethylamine, diisopropylethylamine, tri-n-propylamine, tri-n-butylamine, benzyldimethylamine, phenethyldimethylamine, N-methylmorpholine, 1,8-diazabicyclo[5.4.0]undec-7-ene, 1,5-diazabicyclo[4.3.0]-non-5-ene or 1,4-diazabicyclo[2.2.2]octane. Examples of the solvent include aliphatic hydrocarbons such as hexane, heptane, nonane, decane, ligroin, cyclohexane and petroleum ether; aromatic hydrocarbons such as benzene, toluene, xylene and mesitylene; halogenated aliphatic hydrocarbons such as methylene chloride, chloroform, carbon tetrachloride, 1,2-dichloroethane and 1,2,3-trichloropropane; halogenated aromatic hydrocarbons such as chlorobenzene, dichlorobenzene and benzotrifluoride; ethers such as diethyl ether, diisopropyl ether, methyl tert-butyl ether, dioxane, tetrahydrofuran and ethylene glycol dimethyl ether; and the like, and mixtures. After completing the reaction, for example, by the methods shown below, the objective present compounds can be isolated.

1) The reaction solution is poured into water, that is extracted with an organic solvent, said organic layer is dried and concentrated
2) The reaction solution is concentrated as it is, or as needed, is filtered and the filtrate is concentrated. In addition, it is possible to purify the present compounds by operations such as recrystalization and chromatography.

This method may be modified by known procedures utilizing carbonyldiimidazole in place of the chlorinating agent.

The present compounds have excellent herbicidal activity, and some of them exhibit excellent selectivity between crop plants and unfavorable weeds. The present compounds show a herbicidal efficacy in foliar treatment and soil treatment of fields, for example, against the various kinds of problematic weeds mentioned in the following.

Polygonaceae:
   wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)
Portulacaceae:
   common purslane (*Portulaca oleracea*)
Caryophyllaceae:
   common chickweed (*Stellaria media*)
Chenopodiaceae:
   common lambsquarters (*Chenopodium album*), kochia (*Kochia scoparia*)
Amaranthaceae:
   redfoot pigweed (*Amaranthus retroflexus*), smooth pigweed (*Amaranthus hybridus*)
Crusiferae:
   wild radish (*Raphanus raphanistrum*), wild mustard (*Sinapis arvensis*), shepherdspurse (*Capsella bursapastoris*)
Leguminosae:
   hemp sesbania (*Sesbania exaltata*), sicklepod (*Cassia obtusifolia*), Florida beggarweed (*Desmodium tortuosum*), white clover (*Trifolium repens*)
Malvaceae:
   velvet leaf (*Abutilon theophrasti*), prickly sida (*Sida spinosa*)
Violaceae:
   field pansy (*Viola rafinesquii*), wild pansy (*Viola tricolor*)
Rubiaceae:
   catchweed bedstraw (cleavers) (*Galium aparine*)
Convolvulaceae:
   ivyleaf morningglory (*Ipomoea hederacea*), tall morningglory (*Ipomoea purpurea*), entireleaf morningglory (*Ipomoea hederacea var intergriuscula*), pitted morningglory (*Ipomoea lacunosa*), field bindweed (*Convolvulus arvensis*)
Labiatae:
   purple deadnettle (*Lamium purpureum*), henbit (*Lamium amplexicaule*)

Solanaceae:
   jimsonweed (*Datura stramonium*), black nightshade (*Solanum nigrum*)
Scrophulariaceae:
   persian speedwell (*Veronica persica*), ivyleaf speedwell (*Veronica hederaefolia*)
Compositae:
   common cocklebur (*Xanthium strumarium*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), japanese mugwort (*Artemisia princeps*), tall goldenrod (*Solidago altissima*)
Boraginaceae:
   field forget-me-not (*Myosotis arvensis*)
Asclepiadaceae:
   common milkweed (*Asclepias syriaca*)
Euphorbiaceae:
   sun spurge (*Euphorbia helioscopia*), spotted spurge (*Euphorbia maculata*)
Gramineae:
   barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oats (*Avena fatua*), johnsongrass (*Sorghum halepense*), quackgrass (*Elytrigia repens*), downy brome (*Bromus tectorum*), bermudagrass (*Cynodon dactylon*), fall panicum (*Panicum dichotomiflorum*), Texas panicum (*Panicum texanum*), shattercane (*Sorghum bicolor*)
Commelinaceae:
   common dayflower (*Commelina communis*)
Equisetaceae:
   field horsetail (*Equisetum arvense*)
Cyperaceae:
   rice flatsedge (*Cyperus iria*), purple nutsedge (*Cyperus rotundus*), yellow nutsedge (*Cyperus esculentus*)

Additionally, some of the present compounds do not show a problematic phytotoxicity against important crops such as corn (*Zea mays*), wheat (*Triticum aestivum*), barley (*Hordeum vulgare*), rice (*Oryza sativa*), sorghum (*Sorghum vulgare*), soybean (*Glycine max*), cotton (*Gossypium* spp.), sugar beet (*Beta vulgaris*), peanut (*Arachis hypogaea*), sunflower (*Helianthus annuus*) and canola (*Brassica napus*); gardening plants such as flowering plants and ornamental plants; vegetable crops.

The present compounds can attain effective control of unfavorable weeds in the no-tillage cultivation of crops such as soybean, corn and wheat. Furthermore, some of them do not show a problematic phytotoxicity against crops.

The present compounds have herbicidal activity against various unfavorable weeds as recited below under the flooding treatment on paddy fields.

Gramineae:
   early watergrass (*Echinocholoa oryzoides*)
Scrophulariaceae:
   Common falsepimpernel (*Lindernia procumbens*)
Lythraceae:
   Indian toothcup (*Rotala indica*), *Ammannia multiflora*
Elatinaceae:
   water wort (*Elatine triandra*)
Cyperaceae:
   smallflower umbrellaplant (*Cyperus difformis*), hardstem bulrush (*Scirpus juncoides*), needle spikerush (*Eleocharis acicularis*), water nutgrass (*Cyperus serotinus*), water chesnut (*Eleocharis kuroguwai*)
Pontederiaceae:
   monochoria (*Monochoria vaginalis*)
Alismataceae:
   arrowhead (*Sagittaria pygmaea*), *Sagittaria trifolia*, waterplantain (*Alisma canaliculatum*)
Potamogetonaceae:
   roundleaf pondweed (*Potamogeton distincutus*)
Umbelliferae:
   watercelery (*Oenanthe javanica*)

Furthermore, some of the present compounds do not show a problematic phytotoxicity against transplanted paddy rice.

The present compounds can attain effective control of various unfavorable weeds in orchards, pastures, lawns, forests, waterways, canals, or other non-cultivated lands.

The present compounds also have herbicidal activity against various aquatic plants such as water hyacinths (*Eichornia crassipes*) which grow in waterways, canals and the like.

The present compounds have substantially the same characteristics as those of the herbicidal compounds described in the publication of International Patent Application, WO95/34659. In the case where crops with tolerance imparted by introducing a herbicide tolerance gene described in the publication are cultivated, the present compounds can be used at greater doses than those used when ordinary crops without tolerance are cultivated, and it is, therefore, possible to attain effective control of other unfavorable plants.

When the present compounds are used as active ingredients of herbicides, they are usually mixed with solid or liquid carriers or diluents, surfactants, and/or other formulation auxiliary agents, and formulated into such as emulsifiable concentrates, wettable powders, flowables, granules, concentrated emulsions, and water-dispersible granules.

These formulations may contain any of the present compounds as an active ingredient at an amount of 0.001% to 80% by weight, preferably 0.005% to 70% by weight, based on the total weight of the formulation.

Example of the solid carrier or diluent may include fine powders or granules of the following materials: mineral matters such as kaolin clay, attapulgite clay, bentonite, terra abla, pyrophyllite, talc, diatomaceous earth and calcite, organic substances such as walnut shell powder, water soluble organic substances such as urea, inorganic salt such as ammonium sulfate, and synthetic hydrated silicon dioxide. Examples of the liquid carrier or diluent may include the following materials:aromatic hydrocarbons including alkylbenzenes such as methylnaphthalene, phenylxylylethane, and xylene alcohols such as isopropyl alcohol, ethylene glycol and 2-ethoxyethanol, esters such as phthalic acid dialkyl ester, ketones such as acetone, cyclohexanone and isophorone, mineral oils such as machine oil, vegetable oils such as soybean oil and cotton seed oil, dimethylsulfoxide, N,N-dimethylformamide, acetonitrile, N-methylpyrrolidone water, and the like.

Examples of the surfactant utilized for emulsification, dispersing or spreading may include the following materials:anionic surfactants such as alkylsulfate ester salts, alkylsulfonate salts, alkylarylsulfonate salts, dialkyl sulfosuccinate salts and polyoxyethylenealkylaryl ether phosphate ester salts, nonionic surfactants such as polyoxyethylene-alkyl ethers, polyoxyethylenealkylaryl ethers, polyoxyethylenepolyoxypropylene block copolymers, sorbitan fatty acid esters and polyoxyethylenesorbitan fatty acid esters; and the like.

Examples of the formulation auxiliary agents may include the following materials: ligninsulfonate salts, alginate salts, polyvinyl alcohol, gum arabic, CMC (carboxymethyl cellulose), PAP (acidic isopropylphosphate), and the like.

The present compounds are usually formulated and applied for the pre- or post-emergence soil, foliar, or flooding treatment of unfavorable weeds. The soil treatment may include soil surface treatment and soil incorporation treatment. The foliar treatments may include application over the plants and directed application in which a chemical is applied only to the unfavorable weeds so as to keep off the crops.

When the present compounds are used as active ingredients of herbicides, the application amount is usually in the range of 0.01 to 10,000 g, preferably 1 g to 8,000 g per hectare, although it may vary depending upon the weather conditions, formulation type, application timing, method of application, soil conditions, objective crop and objective unfavorable weed(s). In the case of emulsifiable concentrates, wettable powders, suspensible concentrates, concentrated emulsions, water dispersable granules, or the like, the formulation is usually applied at prescribed amounts after diluted with 10 L to 1,000 L of water (in which an adjuvant such as a spreading agent may be added, if necessary) per hectare. In the case of granules or certain types of suspensions, the formulation is usually applied as such without any dilution.

Example of the adjuvant used, if necessary, may include in addition to the surfactants described above, polyoxyethylene resin acids (esters), ligninsulfonate salts, abietate salts, dinaphthylmethanedisulfonate salts, crop oil concentrate, vegetable oils such as soybean oil, corn oil, cotton seed oil and sunflower oil.

The present compounds may be used in the places such as corn fields, wheat fields, barley fields, rice fields, sorghum fields, soybean fields, cotton fields, sugar beet fields, peanut fields, sunflower fields, rape fields and paddy fields.

The present compounds can also be utilized as active ingredients of harvest-aids such as desiccants and defoliants agents for cottons, desiccants of potatoes (*Solanum tuberosum*). In these cases, the present compounds are usually formulated in the same manner as the case where they are used as active ingredients of herbicides, and used alone or in combination with other harvesting aids for foliar treatment before the harvesting of crops.

EXAMPLES

Hereinafter, the present invention is further explained with the production examples, formulation examples and test examples, but the present invention is not limited such examples.

To begin with, the production examples of the present compounds are explained.

Production Example 1

Seventeen grams (17.0 g) of the hydroxy compound of formula (II), 8.0 g of methyl S-lactate (Merck & Co., Inc.) and 20.0 g of triphenylphosphine were dissolved in 50 mL of tetrahydrofuran. To the solution, a solution which had 13.0 g of diethyl azodicarboxylate dissolved in 15 mL of tetrahydrofuran was added dropwise over 30 minutes while stirring under ice-cooling. At that time, the reaction temperature was kept from 8 to 15° C. Thereafter, and after stirring at room temperature for 30 minutes, the reaction solution was poured into water, and that was extracted with ethyl acetate. The organic layer was washed with saturated sodium chloride solution, and after drying over magnesium sulfate, was concentrated. The residue was subjected to silica gel column chromatography (eluent, hexane/ethyl acetate=3/1), and 18.48 g of methyl (2R)-2-[2-chloro-4-fluoro-5-[3-methyl-2,6-dioxo-4-(trifluoromethyl)-1,2,3,6-tetrahydropyrimidin-1-yl]phenoxy]propionate (hereinafter referred to as the present compound 1) was obtained.

$^1$H-NMR (CDCl$_3$, 300 MHz): δ (ppm) 7.31 (1H, d, J=9.0 Hz), 6.82 (½H, d, J=6.42 Hz), 6.81 (½H, d, J=6.45 Hz), 6.35 (1H, s), 4.68 (1H, q, J=6.9 Hz), 3.74 (3H, s), 3.55 (3H, s, br), 1.66 (3H, d, J=6.9 Hz) $[\alpha]_D^{20}$+25.8° (c 1.0, CH$_3$OH), the content (R isomer:S isomer)=97.3:2.7 (determined by LC method utilizing optically active column).

Production Example 2

Ten grams (10.0 g) of (2R)-2-[2-chloro-4-fluoro-5-[3-methyl-2,6-dioxo-4-(trifluoromethyl)-1,2,3,6-tetrahydropyrimidin-1-yl]phenoxy]propionic acid were dissolved in 150 mL of ethanol. To the solution, 1.0 mL of sulfuric acid was added and refluxed for 3 hours under heating. Thereafter, a part of the reaction solution was collected, concentrated and poured into water, and that was extracted with ethyl acetate. The organic layer was washed with saturated sodium chloride solution, and after drying over anhydrous magnesium sulfate, was concentrated. The residue was subjected to silica gel column chromatography (eluent, hexane/ethyl acetate=3/1), and 7.8 g of ethyl (2R)-2-[2-chloro-4-fluoro-5-[3-methyl-2,6-dioxo-4-(trifluoromethyl)-1,2,3,6-tetrahydropyrimidin-1-yl]phenoxy]propionate (hereinafter referred to as the present compound 2) was obtained.

$^1$H-NMR (CDCl$_3$, 300 MHz): δ (ppm) 7.31 (1H, d, J=9.0 Hz), 6.83 (½H, d, J=6.4 Hz), 6.81 (½H, d, J=6.4 Hz), 6.34 (½H, s), 6.33 (½H, s), 4.67 (1H, q, J=7.0 Hz), 4.25–4.15(2H, m), 3.54 (3H, q, J=1.3 Hz), 1.66 (3H, d, J=7.0 Hz), 1.23 (½×3H, t, J=7.2 Hz), 1.22 (½×3H, t, J=7.1 Hz), R content: 99% or more (determined by LC method utilizing optically active column).

Production Example 3

One and fifty-one hundredths grams (1.51 g) of (2R)-2-[2-chloro-4-fluoro-5-[3-methyl-2,6-dioxo-4-(trifluoromethyl)-1,2,3,6-tetrahydropyrimidin-1-yl]phenoxy]propionic acid was dissolved in 10 mL of tetrahydrofuran, and after adding 1.5 mL of thionyl chloride while stirring, that was heated with stirring under reflux for 1 hour. Thereafter, and after allowing the reaction solution to be cooled, and concentrated, that was dissolved in 6 mL of tetrahydrofuran and 1 mL of pyridine was added thereto, and then, 0.5 mL of allylalcohol was added thereto. After stirring at room temperature for 1 hour, ice-water was poured into the reaction solution. After adding ethyl acetate and saturated sodium chloride solution, and phase separating, the organic layer was washed with saturated sodium chloride solution, and after drying over magnesium sulfate, that was concentrated. The residue was subjected to silica gel column chromatography (eluent, hexane/ethyl acetate=3/1), and 1.02 g of allyl (2R)-2-[2-chloro-4-fluoro-5-[3-methyl-2,6-dioxo-4-(trifluoromethyl)-1,2,3,6-tetrahydropyrimidin-1-yl]phenoxy]propionate (hereinafter, referred to as the present compound 3) was obtained.

$^1$H-NMR (CDCl$_3$, 300 MHz): δ (ppm) 7.31 (1H, d, J=8.9 Hz), 6.84 (½H, d, J=6.50 Hz), 6.82 (½H, d, J=6.41 Hz), 6.34

(1H, s), 5.91–5.80 (1H, m), 5.29 (1H, ddd, J=1.1 Hz, 1.1 Hz, 17.1 Hz), 5.22 (1H, dd, J=1.1 Hz, 10.7 Hz), 4.71 (1H, q, J=7.1 Hz), 4.64 (2H, dd, J=1.1 Hz, 5.6 Hz), 3.55 (3H, t, J=1.45 Hz), 1.68 (3H, d, J=7.1 Hz), $[\alpha]_D^{19}$+24.70° (c 1.0, $CH_3OH$).

Production Example 4

Thirty grams (30.0 g) of the hydroxy compound of formula (II) was dissolved in 360 g of N,N-dimethylformamide, and after adding 36.7 g of potassium carbonate, that was stirred for 100 minutes at room temperature. To the mixture, 18.96 g of isobutyl (S)-2-chloropropionate was added dropwise over 100 minutes, and then the reaction mixture was stirred for 8.75 hours at room temperature. Thereafter, the reaction mixture was poured into ice-water and extracted with ethyl acetate. The organic layer was washed with saturated sodium chloride solution twice, and after drying over magnesium sulfate, that was concentrated. The residue was subjected to silica gel column chromatography (eluent, hexane/ethyl acetate), and 25.28 g of isobutyl (2R)-2-[2-chloro-4-fluoro-5-[3-methyl-2,6-dioxo-4-(trifluoromethyl)-1,2,3,6-tetrahydropyrimidin-1-yl]phenoxy]propionate (hereinafter, referred to as the present compound 4) was obtained.

$^1$H-NMR ($CDCl_3$, 300 MHz): δ (ppm) 7.31 (1H, d, J=8.7 Hz), 6.81 (½H, d, J=6.4 Hz), 6.80 (½H, d, J=6.3 Hz), 4.70 (1H, q, J=6.6 Hz), 3.97–3.86 (2H, m), 3.54 (3H, q, J=1.3 Hz), 1.97–1.82 (1H, m), 1.70 (3H, d, J=6.6 Hz), 0.861 (3H, d, J=6.5 Hz), 0.858 (3H, d, J=6.5 Hz), $[\alpha]_D^{29}$+24.50° (c 1.0, $CH_3OH$).

Production Example 5

Forty-one and a half grams (41.5 g) of the hydroxy compound of the formula (II), 13.5 g of methyl S-lactate (Merck & Co., Inc.; Lot 42111033) and 35.4 g of triphenylphosphine were dissolved in 350 mL of tetrahydrofuran. To the solution, 67.8 g of a 40% toluene solution containing 13.0 g of diisopropyl azodicarboxylate was added dropwise over 15 minutes under ice-cooling. Thereafter, and after stirring at room temperature for 2.75 hours, the reaction solution was poured into water, and that was extracted with ethyl acetate. The organic layer was washed with saturated sodium chloride solution, and after drying over magnesium sulfate, was concentrated. The residue was subjected to silica gel column chromatography (eluent, hexane/ethyl acetate=3/1), and 40.8 g of methyl (2R)-2-[2-chloro-4-fluoro-5-[3-methyl-2,6-dioxo-4-(trifluoromethyl)-1,2,3,6-tetrahydropyrimidin-1-yl]phenoxy]propionate (hereinafter referred to as the present compound 5) was obtained. R content: 99% or more (determined by LC method utilizing optically active column).

Production Example 6

Five grams (5.0 g) of the present compound 5 was dissolved in tetrahydrofuran to prepare a 100 mL solution (hereinafter referred to as the solution A). On the other hand, 5.0 g of the Compound X, that is methyl (2S)-2-[2-chloro-4-fluoro-5-[3-methyl-2,6-dioxo-4-(trifluoromethyl)- 1,2,3, 6-tetrahydropyrimidin-1-yl]phenoxy]propionate, produced by the Reference Production Example 5 below was dissolved in tetrahydrofuran to prepare a 100 mL solution (hereinafter referred to as the solution B).

Nine mililiters (9.0 mL) of the solution A and 1.0 mL of the solution B were combined and then concentrated to give methyl 2-[2-chloro-4-fluoro-5-[3-methyl-2,6-dioxo-4-(trifluoromethyl)-1,2,3,6-tetrahydropyrimidin-1-yl]phenoxy]propionate, the R content of which is 90% (hereinafter referred to as the present compound 6).

Eight mililiters (8.0 mL) of the solution A and 2.0 mL of the solution B were combined and then concentrated to give methyl 2-[2-chloro-4-fluoro-5-[3-methyl-2,6-dioxo-4-(trifluoromethyl)-1,2,3,6-tetrahydropyrimidin-1-yl]phenoxy]propionate, the R content of which is 80% (hereinafter referred to as the present compound 7).

Next, production examples of comparative compounds, which were utilized to compare with the present compounds, are provided as reference production examples.

Reference Production Example 1

Eight and a half grams (8.5 g) of the hydroxy compound of the formula (II), 3.12 g of methyl R-lactate (Tokyo Chemical Industry Co., Ltd.) and 7.9 g of triphenylphosphine were dissolved in 25 mL of tetrahydrofuran. To the solution, a solution which had 5.22 g of diethyl azodicarboxylate dissolved in 5 mL of tetrahydrofuran was added dropwise over 15 minutes under ice-cooling with stirring. At that time, the reaction temperature was kept 8 to 20° C. Thereafter, and after stirring at room temperature for 30 minutes, the reaction solution was poured into water, and that was extracted with ethyl acetate. After the organic layer was dried over magnesium sulfate, such was concentrated. The residue was subjected to silica gel column chromatography (eluent, hexane/ethyl acetate=3/1), and 9.91 g of methyl (2S)-2-[2-chloro-4-fluoro-5-[3-methyl-2,6-dioxo-4-(trifluoromethyl)-1,2,3,6-tetrahydropyrimidin-1-yl]phenoxy]propionate (hereinafter referred to as the comparative compound 1).

$^1$H-NMR ($CDCl_3$, 300 MHz): δ (ppm) 7.31 (1H, d, J=9.0 Hz), 6.82 (½H, d, J=6.42 Hz), 6.81 (½H, d, J=6.45 Hz), 6.35 (1H, s), 4.68 (1H, q, J=6.9 Hz), 3.74 (3H, s), 3.55 (3H, s, br), 1.66 (3H, d, J=6.9 Hz), $[\alpha]_D^{20}$−23.5° (c 1.0, $CH_3OH$), the content (R isomer: S isomer)=2.9:97.1 (determined by LC method utilizing optically active column).

Reference Production Example 2

Twenty grams (20 g) of the hydroxy compound of the formula (II) was dissolved in 200 mL of N,N-dimethylformamide. To the solution, 10.0 g of potassium carbonate and 12.1 mL of ethyl (RS)-2-bromopropionate were added and stirred for 40 minutes at room temperature. Thereafter, the reaction mixture was poured into water, and that was extracted with ethyl acetate. The organic layer was washed with saturated sodium chloride solution and dried over anhydrous magnesium sulfate, such was concentrated. The residue was subjected to silica gel column chromatography (eluent, hexane/ethyl acetate=3/1), and 23.46 g of ethyl (2RS)-2-[2-chloro-4-fluoro-5-[3-methyl-2,6-dioxo-4-(trifluoromethyl)-1,2,3,6-tetrahydropyrimidin-1-yl]phenoxy]propionate (hereinafter referred to as the comparative compound 2).

Reference Production Example 3

One and thirty-two hundredths grams (1.32 g) of (2RS)-2-[2-chloro-4-fluoro-5-[3-methyl-2,6-dioxo-4-(trifluoromethyl)-1,2,3,6-tetrahydropyrimidin-1-yl]phenoxy]propionic acid was dissolved in 15 mL of tetrahydrofuran. To the solution, 1.0 mL of thionyl chloride was added and heated for 70 minutes under reflux. Thereafter, the reaction solution was concentrated to be a volume of 15 mL, to which 1 mL of allyl alcohol and 1 mL of pyridine were added and stirred for 4 hours at room temperature. And then the reaction solution was poured into water, and that was extracted with ethyl acetate. The organic layer was washed with saturated sodium chloride solution and dried over anhydrous magnesium sulfate, such was concentrated. The residue was subjected to silica gel column chromatography (eluent, hexane/ethyl acetate=5/1), and 1.02 g of allyl (2RS)-2-[2-chloro-4-fluoro-5-[3-methyl-2,6-dioxo- 4-(trifluoromethyl)-1,2,3,6-tetrahydropyrimidin-1-yl]phenoxy]propionate (hereinafter referred to as the comparative compound 3).

Reference Production Example 4

Five milliliters (5.0 mL) of the solution A above and 5.0 mL of the solution B were combined and then concentrated to give methyl 2-[2-chloro-4-fluoro-5-[3-methyl-2,6-dioxo-4-(trifluoromethyl)-1,2,3,6-tetrahydropyrimidin-1-yl]phenoxy]propionate, the R content of which is 50% (hereinafter referred to as the comparative compound 4).

Reference Production Example 5

One and thirteen hundredths grams (1.13 g) of the hydroxy compound of the formula (II), 0.4 mL of methyl R-lactate (Tokyo Chemical Industry Co., Ltd.) and 1.0 g triphenylphosphine were dissolved in 7.5 mL of tetrahydrofuran. To the solution, 1.9 g of a 40% toluene solution containing diisopropyl azodicarboxylate was added dropwise over 15 minutes under ice-cooling. Thereafter, and after stirring at room temperature for 1.5 hours, the reaction solution was poured into water, and that was extracted with ethyl acetate. After the organic layer was dried over magnesium sulfate, such was concentrated. The residue was subjected to silica gel column chromatography (eluent, hexane/ethyl acetate=3/1), and 0.91 g of methyl (2S)-2-[2-chloro-4-fluoro-5-[3-methyl-2,6-dioxo-4-(trifluoromethyl)-1,2,3,6-tetrahydropyrimidin-1-yl]phenoxy]propionate (referred to as the Compound X). S content: 99% or more (determined by LC method utilizing optically active column)

Additionally, a production example of a starting material of the present compounds, that is the carboxylic acid compound of the formula (V), is given as reference production example 6.

Reference Production Example 6

Three and one hundredth grams (3.01 g) of methyl (2R)-2-[2-chloro-4-fluoro-5-[3-methyl-2,6-dioxo-4-(trifluoromethyl)-1,2,3,6-tetrahydropyrimidin-1-yl]phenoxy]propionate (the present compound 1) was dissolved in 30 mL of dioxane. To the solution, a mixture of 5 mL of conc. hydrochloric acid and 5 mL of water was added with stirring, and then heated for 2.5 hours under reflux with stirring. Thereafter, after allowing the reaction solution to be cooled to room temperature, ice water were poured into the solution, and further ethyl acetate and saturated sodium chloride solution were added. After phase separation, the organic layer was washed with saturated sodium chloride solution, dried over magnesium sulfate and concentrated. The residue was subjected to silica gel column chromatography (eluent, hexane/ethyl acetate), and 2.42 g of (2R)-2-[2-chloro- 4-fluoro-5-[3-methyl-2,6-dioxo-4-(trifluoromethyl)-1,2,3,6-tetrahydropyrimidin-1-yl]phenoxy]propionic acid.

Next, the formulation examples of the present compounds are explained.

Formulation Example 1

Fifty (50) parts of each of the present compounds 1 to 7, 3 parts of calcium ligninsulfonate, 2 parts of sodium laurylsulfate, and 45 parts of synthetic hydrated silicon dioxide are well pulverized and mixed, to obtain each of the wettable powders.

Formulation Example 2

Ten (10) parts of each of the present compound 1 to 7, 14 parts of polyoxyethylenestyryl phenyl ether, 6 parts of calcium dodecylbenzenesulfonate, 35 parts of xylene, and 35 parts of cyclohexanone are mixed to obtain each of the emulsifiable concentrates.

Formulation Example 3

Two (2) parts of each of the present compound 1 to 7, 2 parts of synthetic hydrated silica, 2 parts of calcium ligninsulfonate, 30 parts of bentonite, and 64 parts of kaolin clay are well pulverized and mixed, and after adding water and well kneading, that is granulated and dried to achieve each of the granules.

Formulation Example 4

Twenty-five (25) parts of each of the present compound 1 to 7, 50 parts of a 10% aqueous solution of polyvinyl alcohol, and 25 parts of water are mixed, are wet pulverized until the average particle diameter is 5 $\mu$m or less, to obtain each of the suspensible concentrates.

Next, test examples are explained to show that the present compounds are effective as an active ingredient of a herbicide.

The herbicidal activity was evaluated at 6 levels with indices of 0 to 5, i.e., designated by the numeral "0", "1", "2", "3", "4" or "5", wherein "0" means that there was no or little difference in the degree of germination or growth between the treated and the untreated tested plants at the time of examination, and "5" means that the test plants died complete or their germination or growth was completely inhibited.

Test Example 1

Foliar Treatment on Upland Fields

Plastic pots which have an area of $(26.5 \times 19) cm^2$ and a depth of 7 cm were filled with upland soil, seeded with common cocklebur (*Xanthium strumarium*) and were given 21 days to grow in a greenhouse. Each of the test compounds was formulated into emulsifiable concentrates according to Formulation Example 2, which was diluted with a designated amount of water containing 1% Agri-Dex (adjuvant produced by Helena Chemical Company), and such was uniformly sprayed over the foliage of the test plants with a sprayer at a volume of 1000 liters per hectare. After the application, the test plants were grown in the greenhouse for 21 days, and the herbicidal activity was examined. Those results are given in Table 1.

TABLE 1

| Test Compound | Application Amount of the Active Ingredient (g/ha) | Herbicidal Activity Common Cocklebur |
|---|---|---|
| Present Compound 1 | 1 | 5 |
| Comparative Compound 1 | 1 | 0 |

As shown in the table above, the present compound (methyl ester, R/S=97.3/2.7) is more effective than the comparative compound (methyl ester, R/S=2.9/97.1).

Test Example 2
Soil Surface Treatment on Upland Fields

Plastic pots which have an area of (26.5×19)cm² and a depth of 7 cm were filled with upland soil, seeded with johnsongrass (*Sorghum halepense*). Each of the test compounds was formulated into emulsifiable concentrates according to Formulation Example 2, which was diluted with a designated amount of water, and such was uniformly sprayed over the soil surface in the pots with a sprayer at a volume of 1000 liters per hectare. After the application, the test plants were grown in a greenhouse for 25 days, and the herbicidal activity was examined. Those results are given in Table 2.

TABLE 2

| Test Compound | Application Amount of the Active Ingredient (g/ha) | Herbicidal Activity johnsongrass |
| --- | --- | --- |
| Present Compound 5 | 16 | 4 |
|  | 32 | 5 |
|  | 63 | 5 |
| Present Compound 6 | 16 | 4 |
|  | 32 | 5 |
|  | 63 | 5 |
| Present Compound 7 | 16 | 4 |
|  | 32 | 5 |
|  | 63 | 5 |
| Comparative Compound 4 | 16 | 1 |
|  | 32 | 2 |
|  | 63 | 4 |

As shown in the table above, the present compounds (methyl ester, the contents of R isomer; 80% or more) are much more effective than the comparative compound (methyl ester, racemic). Especially, a forth dosage (16 g/ha) of the present compound against the dosage of the comparative compound (63 g/ha) showed almost the same effect for controlling the weeds.

Test Example
Soil Incorporation Treatment on Upland Fields

Cylindrical plastic pots of 10 cm in diameter and a 10 cm in depth were filled with upland soil. The soil from the surface to 3 cm in depth was taken and mixed with the dilution which was given by diluting the emulsifiable concentrates of the test compounds, formulated according to Formulation Example 2, with water at a volume of 606 liters per hectare. Thereafter, the treated soil was put back to the pots, in which johnsongrass (*Sorghum halepense*) was sowed at 1.5 cm in depth. The test plants were grown in a greenhouse for 19 days, and the herbicidal activity was examined. Those results are given in Table 3.

TABLE 3

| Test Compound | Application Amount of the Active Ingredient (g/ha) | Herbicidal Activity johnsongrass |
| --- | --- | --- |
| Present Compound 5 | 20 | 4 |
|  | 40 | 5 |
|  | 80 | 5 |
| Present Compound 6 | 20 | 3 |
|  | 40 | 5 |
|  | 80 | 5 |
| Present Compound 7 | 20 | 2 |
|  | 40 | 5 |
|  | 80 | 5 |

TABLE 3-continued

| Test Compound | Application Amount of the Active Ingredient (g/ha) | Herbicidal Activity johnsongrass |
| --- | --- | --- |
| Comparative Compound 4 | 20 | 0 |
|  | 40 | 2 |
|  | 80 | 4 |

As shown in the table above, the present compounds (methyl ester, the contents of R isomer; 80% or more) is much more effective than the comparative compound (methyl ester, racemic).

Test Example 4
Soil Surface Treatment on upland fields

Plastic pots which have an area of (26.5×19)cm² and a depth of 7 cm were filled with upland soil, seeded with hemp sesbania (*Sesbania exaltata*), barnyardgrass (*Echinochloa crus-gali*) and johnsongrass (*Sorghum halepense*). Each of the test compounds was formulated into emulsifiable concentrates according to Formulation Example 2, which was diluted with a designated amount of water, and such was uniformly sprayed over the soil surface in the pots with a sprayer at a volume of 100 liters per hectare. After the application, the test were grown in a greenhouse for 25 days, and the herbicidal activity was examined. Those results are given in Table 4.

TABLE 4

| Test Compound | Application Amount of the Active Ingredient (g/ha) | Herbicidal Activity | | |
| --- | --- | --- | --- | --- |
| | | hemp sesbania | barnyard-grass | johnson-grass |
| Present Compound 2 | 16 | 2 | 5 | 3 |
|  | 32 | 5 | 5 | 5 |
|  | 63 | 5 | 5 | 5 |
| Comparative Compound 2 | 16 | 0 | 0 | 0 |
|  | 32 | 2 | 3 | 2 |
|  | 63 | 3 | 3 | 3 |
|  | 125 | 4 | 5 | 4 |

As shown in the table above, the present compounds (ethyl ester, the contents of R isomer; 99% or more) is much more effective than the comparative compound (ethyl ester, racemic). Especially, a forth dosage (32 g/ha) of the present compound against the dosage of the comparative compound (125 g/ha) showed same or more effective for controlling the weed.

Test Example 5
Soil Incorporation Treatment on Upland Fields

Cylindrical plastic pots of 10 cm in diameter and a 10 cm in depth were filled with upland soil. The soil from the surface to 3 cm in depth was taken and mixed with the dilution which was given by diluting the emulsifiable concentrates of the test compounds, formulated according to Formulation Example 2, with water at a volume of 606 liters per hectare. Thereafter, the treated soil was put back to the pots, in which johnsongrass (*Sorghum halepense*) was sowed at 1.5 cm in depth. The test plants were grown in a greenhouse for 19 days, and the herbicidal activity was examined. Those results are given in Table 5.

TABLE 5

| Test Compound | Application Amount of the Active Ingredient (g/ha) | Herbicidal Activity johnsongrass |
|---|---|---|
| Present Compound 2 | 20 | 4 |
|  | 40 | 5 |
|  | 80 | 5 |
| Comparative Compound 2 | 20 | 1 |
|  | 40 | 2 |
|  | 80 | 4 |

As shown in the table above, the present compounds (ethyl ester, the contents of R isomer; 99% or more) is much more effective than the comparative compound (ethyl ester, racemic). Especially, a forth dosage (20 g/ha) of the present compound against the dosage of the comparative compound (80 g/ha) showed almost the same effect for controlling the weed.

Test Example 6
Soil Surface Treatment on Upland Fields

Plastic pots which have an area of (26.5×19)cm² and a depth of 7 cm were filled with upland soil, seeded with johnsongrass (*Sorghum halepense*). Each of the test compounds was formulated into emulsifiable concentrates according to Formulation Example 2, which was diluted with a designated amount of water, and such was uniformly sprayed over the soil surface in the pots with a sprayer at a volume of 1000 liters per hectare. After the application, the test plants were placed in a greenhouse for 25 days, and the herbicidal activity was examined. Those results are given in Table 6.

| Test Compound | Application Amount of the Active Ingredient (g/ha) | Herbicidal Activity johnsongrass |
|---|---|---|
| Present Compound 3 | 16 | 3 |
|  | 32 | 5 |
|  | 63 | 5 |
| Comparative Compound 3 | 16 | 0 |
|  | 32 | 1 |
|  | 63 | 2 |

As shown in the table above, the present compound is much more effective than the comparative compound. Especially, even a forth dosage ("3" at 16 g/ha) of the present compound is much more effective than the comparative compound ("2" at 63 g/ha).

What is claimed is:

1. An optically active uracil compound of the formula

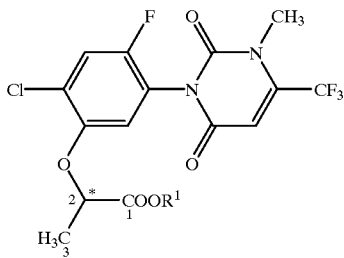

wherein, R¹ represents C1–C8 alkyl or C3–C8 alkenyl and * represents an asymmetric carbon atom whose configuration is R.

2. An optically active uracil compound of the formula:

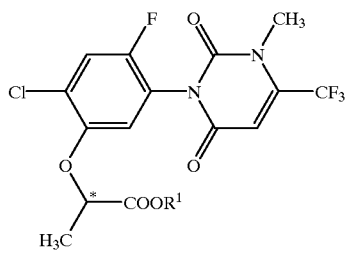

wherein, R¹ represents $C_1$–$C_8$ alkyl or $C_3$–$C_8$ alkenyl and * represents an asymmetric carbon atom whose configuration is R, wherein the optically active uracil compound is an essentially pure R isomer of the absolute configuration in the $2^{nd}$ position of the propionate moiety.

3. The uracil compound according to claim 1, wherein the optically active uracil compound is an R-rich isomer of the absolute configuration in the $2^{nd}$ position of the propionate moiety, wherein R-rich isomer means RS mixture containing 80% or more R isomer based on the RS mixture.

4. The uracil compound according to claim 1, wherein R¹ represents C1–C6 alkyl.

5. The uracil compound according to claim 1, wherein R¹ represents C3–C6 alkenyl.

6. The uracil compound according to claim 2, wherein R¹ represents methyl.

7. The uracil compound according to claim 3, wherein R¹ represents methyl.

8. The uracil compound according to claim 2, wherein R¹ represents ethyl.

9. The uracil compound according to claim 3, wherein R¹ represents ethyl.

10. The uracil compound according to claim 2, wherein R¹ represents allyl.

11. The uracil compound according to claim 3, wherein R¹ represents allyl.

12. The uracil compound according to claim 2, wherein R¹ represents isobutyl.

13. The uracil compound according to claim 3, wherein R¹ represents isobutyl.

14. A herbicidal composition which comprises the uracil compound described in claim 1 as an active ingredient, and a diluent or a carrier.

15. A herbicidal composition which comprises the uracil compound described in claim 2 as an active ingredient, and a diluent or a carrier.

16. A herbicidal composition which comprises the uracil compound described in claim 3 as an active ingredient, and a diluent or a carrier.

17. A method for controlling weeds which comprises applying an effective amount of the uracil compound described in claim 1 to weeds or a place where weeds grow or will grow.

18. A method for controlling weeds which comprises applying an effective amount of the uracil compound described in claim 2 to weeds or a place where weeds grow or will grow.

19. A method for controlling weeds which comprises applying an effective amount of the uracil compound described in claim 3 to weeds or a place where weeds grow or will grow.

* * * * *